United States Patent [19]
Schwan

[11] 3,939,165
[45] Feb. 17, 1976

[54] 5,6,6a,6b,7,8-HEXAHYDROBENZ[a]-PHENANTHRIDINE HYDROCHLORIDE

[75] Inventor: Thomas J. Schwan, Norwich, N.Y.

[73] Assignee: Morton-Norwich Products, Inc., Norwich, N.Y.

[22] Filed: Nov. 14, 1974

[21] Appl. No.: 523,589

[52] U.S. Cl...... 260/286 R; 260/283 R; 260/286 A; 424/258
[51] Int. Cl.² .................................... C07D 215/58
[58] Field of Search ........ 260/286 R, 286 A, 283 R, 260/283 SY

[56] References Cited
UNITED STATES PATENTS

| | | |
|---|---|---|
| 3,435,038 | 3/1969 | Hardtmann et al. ............ 260/286 R |
| 3,549,644 | 12/1970 | Shavel ............................. 260/286 R |
| 3,639,411 | 2/1972 | Albertson et al. ............ 260/283 SY |
| 3,790,576 | 2/1974 | DeWald ....................... 260/283 SY |

OTHER PUBLICATIONS

Walker, "J.A.C.S." 76, 3999–4003, 1954.

*Primary Examiner*—Richard J. Gallagher
*Assistant Examiner*—David E. Wheeler
*Attorney, Agent, or Firm*—Anthony J. Franze

[57] ABSTRACT

A compound 5,6,6a,6b,7,8-hexahydrobenz[a]phenanthridine hydrochloride of the formula possesses pharmacological activity as an antidepressant.

1 Claim, No Drawings

5,6,6A,6B,7,8-HEXAHYDROBENZ(A)PHENAN-THRIDINE HYDROCHLORIDE

This invention relates to a chemical compound. In particular it is concerned with a compound of the formula:

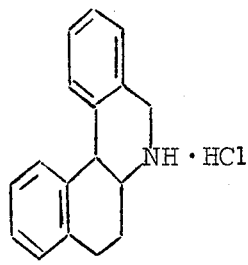

This compound possesses pharmacological activity affecting the central nervous system. When administered perorally to animals, it exhibits antidepressant action. Its antidepressant property is evidenced in the control of tetrabenazine induced ptosis in mice. An oral dose of 50 mg/kg of this compound to mice intraperitoneally receiving 35 mg/kg of tetrabenazine counteracts the ptosis producing property of tetrabenzaine.

In order that this invention be readily available to and understood by those skilled in the art, the following example is supplied.

5,6,6a,6b,7,8-Hexahydrobenz[a]phenanthridine hydrochloride

To 587 g of polyphosphoric acid stirred at 60°–70° was added quickly 34.5 g (0.119 mole) of 2-benzylamine-1,2,3,4-tetrahydro-1-naphthol hydrochloride. The mixture was stirred at 95°–100° on a steam bath for 20 hours and poured into 2000 g stirred ice water. The mixture was stirred for 2.0 hours and filtered through paper. The solid isolated, wt. 18.8 g., was discarded.

The yellow filtrate was maintained at 20°–55° while 737 g solid KCH was added to pH>10. The mixture was extracted with 3 × 400 ml $CHCl_3$. The combined extracts were dried over $MgSO_4$ and concentrated to dryness in vacuo to give 16.5 g of an oil.

The oil was dissolved in 85 ml absolute ethanol and 30 ml ethanolic hydrogen chloride was added to give after cooling 8.30 g of crude product. Recrystallization from methanol gave 3.80 g (12%) of the product, m.p. 304°–315°. Further recrystallization from methanol gave the analytical sample, m.p. 305°–310°.

Anal. Calcd. for $C_{17}H_{17}N \cdot HCl$: C, 75.12; H, 6.67; N, 5.15. Found: C, 74.84; H, 6.73; N, 5.01.

What is claimed is:
1. A compound of the formula:

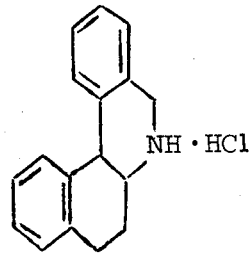

* * * * *